(12) United States Patent
Pisano et al.

(10) Patent No.: US 6,897,235 B2
(45) Date of Patent: May 24, 2005

(54) COMPOSITIONS USEFUL FOR THE TREATMENT OF PATHOLOGIES RESPONDING TO THE ACTIVATION OF PPAR-γ RECEPTOR

(75) Inventors: Claudio Pisano, Rome (IT); Teresa Riccioni, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 10/471,786

(22) PCT Filed: Mar. 1, 2002

(86) PCT No.: PCT/IT02/00127

§ 371 (c)(1),
(2), (4) Date: Sep. 16, 2003

(87) PCT Pub. No.: WO02/074291

PCT Pub. Date: Sep. 26, 2002

(65) Prior Publication Data

US 2004/0092540 A1 May 13, 2004

(30) Foreign Application Priority Data

Mar. 15, 2001 (IT) .................................... RM2001A0136

(51) Int. Cl.$^7$ .............................................. A61K 31/35
(52) U.S. Cl. ..................................................... 514/451
(58) Field of Search ................................. 549/264, 305; 514/462, 470, 451

(56) References Cited

FOREIGN PATENT DOCUMENTS

| WO | WO 00/50414 | 8/2000 |
| WO | WO 01/68070 | 9/2001 |

OTHER PUBLICATIONS

Patent Abstracts of Japan, vol. 1998, No. 05, Apr. 30, 1998 & JP 10–007557 A (Banyu Pharmaceut Co., Ltd.) Jan. 13, 1998.

Database WPI, Section Ch, Week 199601, Derwent Publications Ltd., London GB; AN 1996–006892, XP002223650 & JP 07 285862 A (Kokka Iyaku Kanrikyoku Shikawa Kokinso) Oct. 31, 1995.

Visant et al.; "All–Trans Retinoic Acid Potentiates Megakaryocyte Colony Formation: In Vitro and In Vivo Effects after Administration to Acute Promyelocytic Leukemia Patient," Leukemia, Macmillan Press Ltd., vol. 8, No. 12, Dec. 1994, pp. 2183–2187.

Yasuhiro et al., Database Biosis Online!, Biosciences Information Service, "Inhibition of Growth and Induction of Apoptosis by All–Trans Retinoic Acid in Lymphoid Cell Lines Transfected with the PML/RAR–Alpha Fusion Gene", Database Accession No. PREV199699105088 XP002223648.

Findley et al., "Effect of Retinoic–Acid on the Clonal Growth of Childhood Myeloid and Lymphoid Leukemias a Pediatric Oncology Group Study", Database Biosis Online!, Biosciences Information Service, Philadelphia, PA, 1984, Database Accession No. PREV198579069170 XP002223649.

Shappell et al., 15S–Hydroxyeicosatetranenoic Acid Activates Peroxisome Proliferator–Activated Receptor Gamma and Inhibits Proliferation in PC3 Prostate Carsinoma Cells:, Cancer Research, vol. 61, No. 2, Jan. 15, 2001, pp. 497–503.

Nanjoo et al., "A New Ligand For the Peroxisome Proliferator–Activated Inhibits Rat Mammary Carcinogenesis", Cancer Research, vol. 59, No. 22, Nov. 15, 1999, pp. 5671–5673.

*Primary Examiner*—Amelia A. Owens
(74) *Attorney, Agent, or Firm*—Nixon & Vanderhye P.C.

(57) ABSTRACT

This invention features the use of the spirolaxine of formula (I) for the treatment of those pathologies responding to the activation of the PPARγ receptor, such as the Type 2 insulin-resistant diabetes. This invention also features a pharmaceutical composition in which the spirolaxine of formula (I) acts as active principle in association with the all-trans retinoic acid of formula (II) for the treatment of those pathologies responding to the activation of the PPARγ receptor, such as the acute malignant haemopathies.

1 Claim, 2 Drawing Sheets

Figure 1:
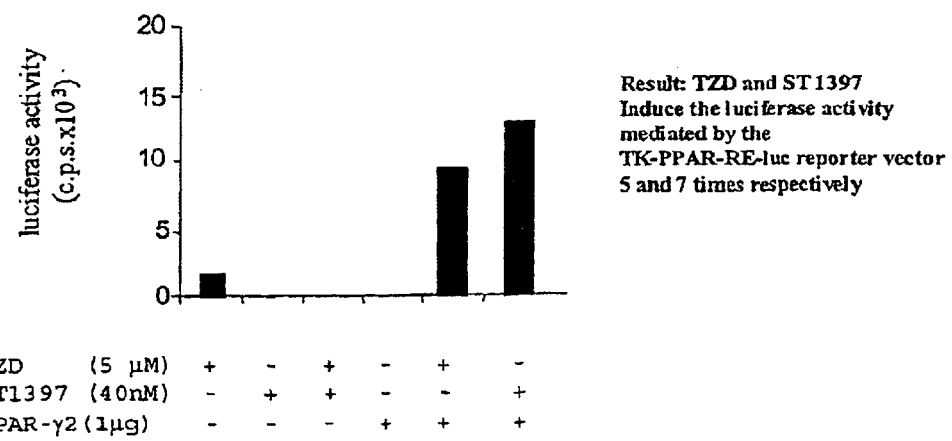

Method:
Plasmids: TK-PPAR-RE luc (2μg), PPARγ 2 (1μg)
Cells: NIH 3T3 ($10^6$)
Transfection by Lipofectamine-Plus (4 h, 37°C, 5% $CO_2$, without serum)
Treatment with TZD (5μM) or ST1397 (40 nM) 24 h before the assay of the luciferase activity.

Result: TZD and ST1397 Induce the luciferase activity mediated by the TK-PPAR-RE-luc reporter vector 5 and 7 times respectively Effect of the association according to the invention on the differentiation of NB4 cells.

COMPOSITIONS USEFUL FOR THE TREATMENT OF PATHOLOGIES RESPONDING TO THE ACTIVATION OF PPAR-γ RECEPTOR

This application is the U.S. national phase of international application PCT/IT02/00127, filed Mar. 1, 2002, which designated the U.S.

The present invention relates to the use of the spirolaxine in treating those pathologies responding to the activation of the PPARγ receptor (peroxisome proliferator activated receptor), such as the Type 2 insulin-resistant diabetes.

The present invention also relates to a pharmaceutical composition, which comprises the spirolaxine associated with the all-trans retinoic acid as an active principle for the treatment of those pathologies responding to the activation of the PPARγ receptor, such as the acute malignant haemopathies.

The PPARγ is a member of the nuclear receptor superfamily. It hetero-dimerizes with the retinoid X receptor (RXR) and acts as a transcriptional regulator of the genes linked to the glucose and lipid metabolism (Diabetes 47(4):507- Apr. 14, 1998).

The diabetes mellitus is a syndrome resulting from the interaction of hereditary and environmental factors; it is characterized by disturbances in insulin secretion and other metabolic and vascular abnormalities, i.e. an elevated concentration of glucose in the blood, non-specific accelerated arteriosclerosis, neuropathy and thickening of the capillary basal lamina caused by a degeneration of the kidney and the retina.

According to a modern classification, the diabetes is divided into two main categories:

1—Insulin-dependent diabetes mellitus (also known as Type 1 diabetes); patients with this type of diabetes literally depend on insulin to prevent ketoacidosis and death. As far as the endogenous insulin secretion is concerned, patients with Type 1 diabetes mellitus exhibit insulinopenia.

2—Noninsulin-dependent diabetes mellitus (also known as Type 2 diabetes); patients with this type of diabetes do not need insulin to live: they can decide whether using it or not to control the symptoms of the diabetes. As far as the endogenous insulin secretion is concerned, patients with Type 2 diabetes can be further classified into two groups. In the first group, insulin levels are either normal or lower than normal; in the second group, insulin values are higher than normal and patients exhibit insulin resistance.

As mentioned above, the PPARγ also acts as a transcriptional regulator of the genes linked to lipid and glucose metabolism.

Insulin-sensitizing medications, ligands of PPARγ, which are used for the treatment of diabetes, are already known.

For example, thiazo-lidinedione derivatives are described as agents useful for the treatment of patients with Type 2 insulin-resistant diabetes mellitus. These compounds are high affinity ligands for PPARγ; their anti-diabetic action in vivo is due to their high link affinity with the said receptor (Nippon Rinsho 2000 February; 58(2):401–4).

Similarly, the PPARγ is expressed at high levels in several leukaemic cell lines, whose inability to differentiate brings to a consequent accumulation at the most immature levels (Jan, Exp. 4, 281–99, 1995).

The acute malignant haemopathies are blood cancers, which are progressively and constantly growing among the populations of the developed countries.

More and more pollutant compounds are present in the air, which cause mutations in the human gene pool. These mutations are often the cause of both solid cancers and malignant haemopathies.

As mentioned above, the acute malignant haemopathies are characterized by the inability of the lymphoid or myeloid line cells to differentiate, which brings to a consequent accumulation at the most immature levels.

Medicaments that can either eliminate these tumoral cells or induce their terminal differentiation are commonly used to treat these pathologies (differentiative therapy).

Ligands of PPARγ with antiproliferative activity are described in the European Journal of Cell Biology 67, 379–85—August 1995 and European Journal of Cell Biology 77, 214–19—November 1998, which show a strong pro-differentiative synergy on different myeloid leukaemic cell lines when associated with retinoids.

In fact, by heterodimerizing with the RXT retinoid receptor, the PPARγ determines an increase in the activity of the activated receptorial complex and the simultaneous activation of both receptors (Cell Vol. 93, 241–52, April 1998).

The combined therapy with retinoic acid and ligands of PPARγ provides a therapeutic advantage for the treatment of those pathologies characterized by the lack of cellular differentiation, such as acute malignant haemopathies.

The spirolaxine is a known compound; it was described in Phytochemistry, (1990) Vol. 29, No 2, pages 613–616, as a metabolite of the fungus *Sporotrichum laxum*. The antitumoral activity of the spirolaine is reported in the Japanese patent application No JP 08177033. The experimental models described in this application refer to in vitro tests on the inhibition of the proliferation of tumoral lines. The tests show that the proliferation is significantly inhibited by direct citotoxicity on the tested tumoral lines.

In WO 9605204, the spirolaxine is described as a compound useful for the treatment of gastroduodenal diseases caused by *Helicobacter pylori*.

In the Japanese patent application No JP 94-82785, the spirolaxine is described as a lipid-lowering compound with anti-cholesterolemic activity.

The procedure for the preparation of the spirolaxine is described in Phytochemistry, (1990) Vol. 29, No 2, pages 613–616.

The retinoic acid is a known compound too. The toxicological and teratogenic profiles of this compound were published by J. J. Kamm in J.Am. Acad. Dermatol. 6, 652 (1982). The synthesis of this compound was described by C. D. Robertson et al. in J. Am. Chem. Soc. 77, 4111 (1955).

The spirolaxine, either alone or in association with the all-trans retinoic acid, was never described as an agent useful for the treatment of those pathologies responding to the activation of the PPARγ receptor.

Thanks to its capacity of stimulating the differentiation of the promyelocytes of tumoral cellular clones (differentiative therapy), the retinoic acid is an agent useful for the treatment of the acute promyelocytic leukemia (APL), a particular type of malignant haemopathy.

Compared with the other types of leukemia, the APL shows less marked leukocytosis, anemia and thrombocytopenia, as well as smaller remission percentage and higher mortality rates when treated with the conventional chemotherapics.

The APL is characterized by an anomalous translocation, which involves the long arm of chromosome 15 and 17 [translocation t(15;17)] involving the gene of the retinoic acid receptor alpha (Cin. Lab. Sci. 2000 Spring; 13(2):106–16).

The oral administration of ATRA induces complete remission in the majority of patients with APL. In some cases, however, treatment with ATRA can cause the so-called "retinoic acid syndrome". This syndrome is characterized by a rapid and progressive increase of the leucocyte counts in the treated patients and is treated by other chemotherapics.

Furthermore, since during the treatment with ATRA the tumoral cells become progressively resistant to this compound, a post-remission therapy is necessary.

Despite efforts made in recent years, there is still a great need for new compounds, either alone or in association, which can be useful for the treatment of those pathologies responding to the activation of the PPARγ receptor.

It has been found that the spirolaxine of formula (I)

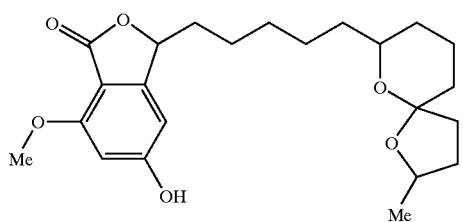

(I)

is an agent useful for the preparation of a medicament to treat those pathologies responding to the activation of the PPARγ receptor.

One object of the present invention is the use of the spirolaxine of formula (I) for the preparation of a medicament to treat those pathologies responding to the activation of the PPARγ receptor, wherein the pathology responding to the activation of such receptor is the Type 2 insulin-resistant diabetes mellitus.

A further object of the invention is a pharmaceutical composition comprising the spirolaxine of formula (I) as active principle

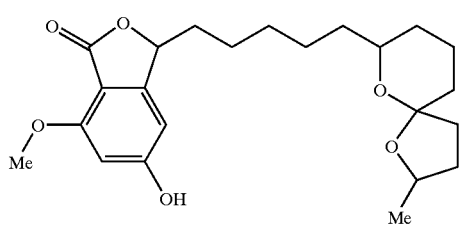

(I)

in association with the all-trans retinoic acid of formula (II)

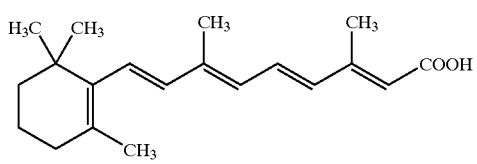

(II)

for the treatment of those pathologies responding to the activation of the PPARγ receptor.

A further object of the invention is the association of the formula (I) spirolaxine with the all-trans retinoic acid of formula (II).

A further object of the invention is a pharmaceutical composition comprising the spirolaxine of formula (I) as an active principle, in association with the all-trans retinoic acid of formula (II) and at least an excipient and/or vehicle.

A further object of the invention is the use of spirolaxine of formula (I) in association with the all-trans retinoic acid of formula (II) for the preparation of a medicament to treat those pathologies responding to the activation of the PPARγ receptor, wherein the pathology responding to the activation of PPARγ is an acute malignant haemopathy included in the group consisting of: lymphoid leukemia, myeloid leukemia, monocytic leukemia and megakaryoblastic leukemia.

A further object of the invention is the use of the spirolaxine of formula (I) in association with the all-trans retinoic acid of formula (II) for the preparation of a medicament to treat the acute promyelocitic leukemia.

Furthermore, the use of therapeutical protocols in which more antitumoral medicaments are administered either at the same time or sequentially is known in the medicine field.

The necessity of administering more antitumoral medicaments within therapeutical protocols is justified by the fact that, by acting at different metabolic levels, in some cases they can contribute to the complete remission of the cancer, while in other cases they can help the treated patients to live longer and/or improve their quality of life. The association in according to the present invention can be used together with one or more known antitumoral medicaments for the treatment of acute malignant haemopathies.

Therefore, a further object of the invention is also a pharmaceutical composition comprising the spirolaxine of formula (I) in association with the all-trans retinoic acid of formula (II) combined with one or more known antitumoral medicaments for the treatment of acute malignant haemopathies. The above-mentioned known antitumoral medicaments are included in the group comprising: alkilating agents; topoisomerase inhibitors; antitubulinic drugs; intercalants; antimetabolites; natural products such as vinca alcaloids, epipodophyllotoxines, antibiotics, enzymes and taxanes.

Experimental data are reported below to better illustrate the invention.

EXAMPLE 1

Activation of the PPARγ by the Spirolaxine (ST 1397)

The capacity of the spirolaxine to link the PPARγ receptor and determine the activation of those genes, which have a PPAR-γ (PPAR-γ RE) responsive sequence was put into evidence through some cellular transfection experiments with a plasmid expressing the PPAR-γ and a reporter vector encoding a gene for luciferase, which is under PPAR-γ RE control (Cell 68; 879–887;1992; J. Biol. Chem. 272; 25252–25259; 1997).

The activation of the expression of the luciferase was put into evidence by transfecting the NIH-3T3 murine fibroblasts with the PPAR-γ plasmid and the TK-PPAR-Reluc reporter vector; the luciferase activity was measured after 24 hour-treatment with the spirolaxine at a concentration of 40 nM.

The activity of the spirolaxine was compared to the activity of a known compound used for the treatment of the Type 2 insulin-resistant diabetes mellitus: the troglitazone (TZD), tested at a concentration of 5 μM.

The results, illustrated in FIG. 1, show that the spirolaxine is more active than the afore-mentioned antidiabetes compound. In fact, the luciferase activity inducted by the reference compound and mediated by the TK-PPAR-Reluc reporter vector (as an index of activation of the receptor) was five times higher than the control, while the luciferase activity induced by the spirolaxine according to the invention was seven times higher than the control.

EXAMPLE 2

Effect of the Association According to the Invention on the Differentiation of a Cellular Line of Human Promyelocitic Leukemia (NB4)

The pro-differentiative activity of the spirolaxine (ST 1397) and the ATRA, both alone and in association, was assessed in this experimental model.

It is well known that the all-trans retinoic acid becomes active at concentrations ranging between 0.1 and 1 μM; the differentiative peak effect is normally observed within the third/fourth day of treatment, when growth stops significantly.

NB4 cells were grown in 25 cm$^2$ flasks at a density of approx 100,000 cells/ml in 5 ml of RPMI 1640 culture with 10% fetal calf serum (FCS). After one day, the cells were treated with ATRA at a concentration of $10^{-7}$ M, or with ST 1397 at doses of 0,1, 0,5 and 1 μM, or with equivalent volumes of the two compounds in association. Then, the cells were put into the incubator for 2–3 days, without replacing the culture medium.

At the end of the second or third day of treatment, the differentiation of the cells into granulocytes was measured by the NBT dye reduction and the spectrophotometric assay of the samples.

The retinoic acid was dissolved in the culture medium with a solution of DMSO 1 mM. Control cultures were treated with equivalent volumes of DMSO, since this compound (DMSO) can be differentiating in certain experimental conditions.

To measure the differentiative effect, 500,000 cells have been gathered from each sample, centrifuged and re-suspended in 1 ml of RPMI 1640 culture with 10% serum, 1 mg/ml of nitroblue tetrazolium (NBT) and 100 ng of PMA. The re-suspended cells were incubated at 37° C. for 20–60 min. At the end of incubation, the cells were centrifuged and the pellet thus obtained was re-suspended in 1 ml of PBS containing 10% Triton X 100.

The samples were sonicated to complete lysis and then read with a spectrophotometer at a wave length of 540 nm.

Figure 2:
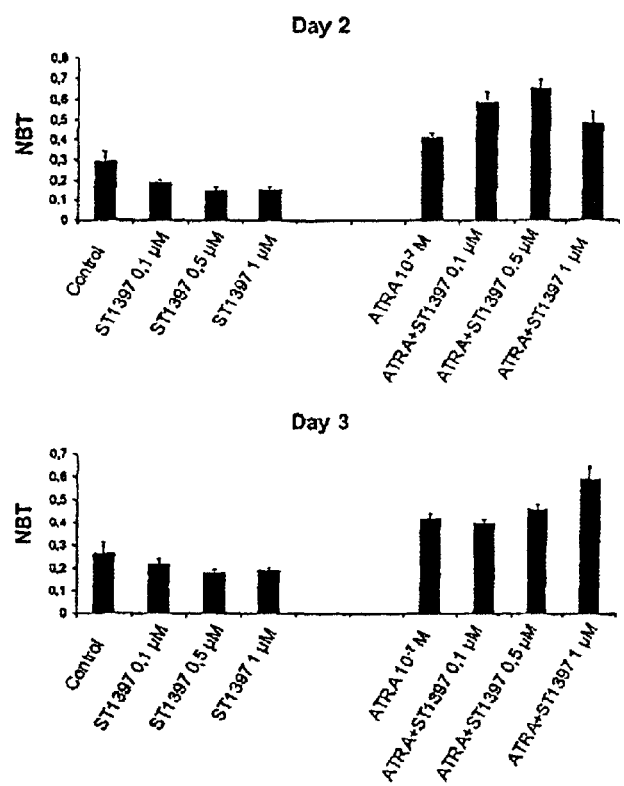

The results, illustrated in FIG. 2, show that the ST1397 does not induce differentiation in NB4 cells, when administered alone. ATRA differentiative effect was already well known, but it was found that this effect was enhanced by the simultaneous administration of ST1397, which is inactive when used alone, as mentioned above.

What is claimed is:

1. A method of treating Type 2 insulin-resistant diabetes mellitus comprising administering to a subject an effective amount of a spirolaxine of formula (I)

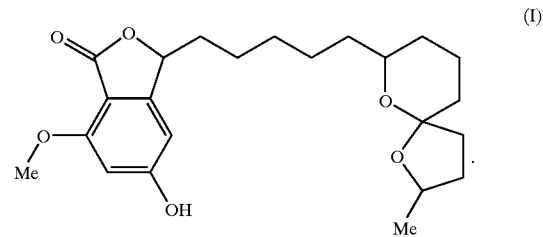

(I)

* * * * *

UNITED STATES PATENT AND TRADEMARK OFFICE
CERTIFICATE OF CORRECTION

PATENT NO.     : 6,897,235 B2
DATED          : May 24, 2005
INVENTOR(S)    : Pisano et al.

It is certified that error appears in the above-identified patent and that said Letters Patent is hereby corrected as shown below:

Title page,
Item [30], should read -- Foreign Application Priority Data, March 16, 2001 (IT) RM2001A0136 --.

Signed and Sealed this

Sixteenth Day of August, 2005

JON W. DUDAS
*Director of the United States Patent and Trademark Office*